(12) United States Patent
Yoon et al.

(10) Patent No.: US 8,922,274 B2
(45) Date of Patent: Dec. 30, 2014

(54) BIOAMPLIFIER FOR NEURAL INTERFACES

(75) Inventors: Euisik Yoon, Superior Township, MI (US); Sun-Il Chang, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 605 days.

(21) Appl. No.: 13/125,165

(22) PCT Filed: Oct. 20, 2009

(86) PCT No.: PCT/US2009/061221
§ 371 (c)(1),
(2), (4) Date: Apr. 20, 2011

(87) PCT Pub. No.: WO2010/048107
PCT Pub. Date: Apr. 29, 2010

(65) Prior Publication Data
US 2011/0193633 A1    Aug. 11, 2011

Related U.S. Application Data (60) Provisional application No. 61/106,852, filed on Oct. 20, 2008.

(51) Int. Cl.
*H03F 1/02*    (2006.01)
*A61B 5/048*    (2006.01)
*A61B 5/00*    (2006.01)

(52) U.S. Cl.
CPC .............. *A61B 5/048* (2013.01); *A61B 5/6846* (2013.01)
USPC .............................................. 330/9; 327/124

(58) Field of Classification Search
USPC .............. 330/9, 302, 303, 304, 305; 327/124, 327/307
See application file for complete search history.

(56) References Cited

U.S. PATENT DOCUMENTS

| | | | |
|---|---|---|---|
| 6,573,785 B1 * | 6/2003 | Callicotte et al. ................. 330/9 |
| 6,741,132 B2 * | 5/2004 | Renous et al. ................. 330/260 |
| 6,996,435 B2 | 2/2006 | Baru Fassio | |
| 7,346,312 B2 | 3/2008 | Irazoqui-Pastor et al. | |
| 7,548,775 B2 | 6/2009 | Kipke et al. | |
| 7,560,969 B2 * | 7/2009 | Chu .............................. 327/307 |
| 7,589,587 B2 * | 9/2009 | Yoshida et al. ................... 330/9 |

(Continued)

FOREIGN PATENT DOCUMENTS

WO    WO2011/028674    3/2011

OTHER PUBLICATIONS

International Search Report for PCT/2009/061221, Jun. 3, 2010, 3 pages.
Written Opinion for for PCT/2009/061221, May 31, 2010, 5 pages.

(Continued)

*Primary Examiner* — Henry Choe
(74) *Attorney, Agent, or Firm* — Reising Ethington P.C.

(57) ABSTRACT

A bioamplifier that includes a high pass filter, open-loop amplifier, and low pass filter in an area efficient design that can be used in implantable neural interfaces. The high pass filter can be implemented by using a switch-capacitance resistor coupled with parasitic capacitance of the electrode. The amplifier can be chopper stabilized and can include a high gain, current-ratio first stage followed by one or more dimension-ratio stages. The low pass filter utilizes the output impedance of the open-loop amplifier to form an embedded $g_m$-C low pass filter.

17 Claims, 6 Drawing Sheets

(56) References Cited

U.S. PATENT DOCUMENTS

| | | | |
|---|---|---|---|
| 7,705,670 B2* | 4/2010 | Chen et al. | 330/9 |
| 7,795,960 B2* | 9/2010 | Lyden et al. | 330/9 |
| 8,497,746 B2* | 7/2013 | Visconti et al. | 333/173 |
| 8,531,239 B2* | 9/2013 | Yamazaki | 330/9 |
| 2004/0155703 A1* | 8/2004 | Ravatin et al. | 330/9 |
| 2006/0033561 A1* | 2/2006 | Perdoor et al. | 330/9 |
| 2006/0066395 A1* | 3/2006 | Elmala et al. | 330/9 |
| 2006/0173259 A1 | 8/2006 | Flaherty et al. | |
| 2007/0244370 A1 | 10/2007 | Kuo et al. | |
| 2009/0212856 A1* | 8/2009 | Chen et al. | 330/9 |
| 2009/0244014 A1 | 10/2009 | Hotelling et al. | |
| 2009/0319211 A1 | 12/2009 | Bresch | |
| 2010/0130844 A1 | 5/2010 | Williams et al. | |
| 2010/0156685 A1 | 6/2010 | Westwick et al. | |
| 2010/0198297 A1 | 8/2010 | Cogan et al. | |

OTHER PUBLICATIONS

Application for PCT/US2010/053449, filed Oct. 20, 2010, 57 pages.

Tim Denison, et al., A 2 µW 100 nV/rtHz Chopper-Stabilized Instrumentation Amplifier for Chronic Measurement of Neural Field Potentials, IEEE Journal of Solid-State Circuits, vol. 42, No. 12, Dec. 2007, 12 pages.

Refet Firat Yazicioglu, et al., A 200µW Eight-Channel Acquisition ASIC for Ambulatory EEG Systems, ISSCC 2008/ Session 81 Medical & Displays/ 8.2, 3 pages, Feb. 2008.

Kofi A. A. Makinwa, et al., A CMOS Temperature-to-Frequency Converter With an Inaccuracy of Less Than ±°0.5 C. (3σ) From—40°C. to 105°C., IEEE Journal of Solid-State Circuits, vol. 41, No. 12, Dec. 2006, 6 pages.

Benoit Gosselin, et al., A Low-Power Integrated Bioamplifier With Active Low-Frequency Suppression, IEEE Transactions on Biomedical Circuits and Systems, vol. 1, No. 3, Sep. 2007, 9 pages.

Reid R. Harrison, et al., A Low-Power Low-Noise CMOS Amplifier for Neural Recording Applications, IEEE Journal of Solid-State Circuits, vol. 38, No. 6, Jun. 2003, 8 pages.

Jeremy Holleman, et al., A Sub-Microwatt Low-Noise Amplifier for Neural Recording, Department of Engineering, University of Washington, 4 pages, Aug. 2007.

Christian C. Enz, et al., An Analytical MOS Transistor Model Valid in All Regions of Operation and Dedicated to Low-Voltage and Low-Current Applications, Analog Integrated Circuits and Signal Processing, 8, 83-114 (1995), 32 pages, Jul. 2005.

Woradorn Wattanapanitch, et al., An Energy-Efficient Micropower Neural Recording Amplifier, IEEE Transactions on Biomedical Circuits and Systems, vol. 1, No. 2, Jun. 2007, 12 pages.

Jayant Parthasarathy, et al., An Integrated CMOS Bio-potential Amplifier with a Feed-Forward DC Cancellation Topology, Proceedings of the 28th IEEE, EMBS Annual International Conference, New York City, Aug. 30-Sep. 3, 2006, 4 pages.

David C. Yates, et al., An Ultra Low Power Low Noise Chopper Amplifier for Wireless EEG, (Invited Paper), Department of Electrical and Electronic Engineering, Imperial College London, 4 pages, Aug. 2006.

\* cited by examiner

BIOAMPLIFIER FOR NEURAL INTERFACES

TECHNICAL FIELD

This invention relates generally to electronic neural interfaces for connecting external electronic devices to neural tissue and, more particularly, to preamplifier circuits incorporated into small scale implantable devices for use in monitoring brain activity.

BACKGROUND OF THE INVENTION

A brain-computer interface (BCI), sometimes called a direct neural interface or a brain-machine interface, provides a direct communication pathway between a human or animal brain (or brain cell culture) and an external device. With advances in CMOS technology, there has been a significant progress in implementing multichannel implantable neural systems which will potentially enable the diagnosis of disease and establishment of a direct interface between brain and external electronic devices. However, chronic monitoring of the brain activities, such as neural spikes, EEG, ECoG, etc., is still a challenge, especially, in wireless ambulatory systems due to constraints in power, noise and area for hardware implementation.

Typically, field potentials (in EEG, ECoG) contain most of their useful information in the bandwidth between 0.5 Hz and 300 Hz with amplitude ranges from 1 μV to 100 μV, where thermal and 1/f noise can severely interfere with the signal. To establish the reliable monitoring of vulnerable neural signals, a front-end preamplifier is typically used and is one of the more significant components in determining the signal-to-noise ratio of the entire system. Preamplifiers should meet the requirements of low noise (<100 nV/√Hz) for reliable measurement of weak signals, low-power consumption (<2 μW) for chronic operation, and small area (<0.1 mm$^2$) for multichannel systems. Furthermore, the interference at the electrode interface induces a DC offset and drift which can be easily up to 1~2V and changes over time at very slow frequency (<0.1 Hz). In at least most cases, this offset must be suppressed to prevent the saturation of the amplifier.

Previously, many preamplifier circuit techniques have been reported in the literature. In order to achieve high noise-power efficiency, most amplifiers utilize closed-loop topologies with input transistors operated in subthreshold region where the $g_m/I_d$ can be maximized. However, these closed-loop amplifiers impose the stability constraint which results in the limit to the power-noise efficiency. A low-power open-loop amplifier has been proposed by J. Holleman and B. Otis, "A Sub-Microwatt Low-Noise Amplifier for Neural Recording," in Engineering in Medicine and Biology Society, 2007. EMBS 2007. pp. 3930-3933. However, the single-ended output is susceptible to common mode noise and supply fluctuation.

To suppress the electrode interface interferences, a simple passive high-pass filter (HPF) is widely utilized using a large input capacitor (10~20 pF) which occupies most areas in the preamplifier. To address this, several other low-frequency suppression techniques have been introduced. However, the low-frequency corners of these amplifiers are not controllable. As reported in J. Parthasarathy, A. G. Erdman, A. D. Redish, and B. Ziaie, "An Integrated CMOS Bio-potential Amplifier with a Feed-Forward DC Cancellation Topology," in Engineering in Medicine and Biology Society, 2006. EMBS '06. 28th Annual International Conference of the IEEE, 2006, pp. 2974-2977, a feed-forward method can be implemented in a small area by using a high-pass filter (HPF) with a low cut-off frequency (~0.5 Hz). However, the cut-off frequency can be difficult to control and vulnerable to process variations.

Thus, there remains a need for an area efficient bioamplifier that exhibits low noise with a good linear gain that is substantially independent of current supply variations.

SUMMARY OF THE INVENTION

In accordance with one aspect of the invention, there is provided a bioamplifier that includes a high pass filter, open-loop amplifier, and low pass filter. The input high pass filter can be implemented in various ways, such as by using a switch-capacitance resistor coupled with parasitic capacitance of the electrode to implement an area efficient high pass filter. The amplifier can also be implemented in various ways, including by use of a high gain, current-ratio first stage followed by one or more dimension-ratio stages. The amplifier can be chopper stabilized if desired or needed for a particular application.

In accordance with another aspect of the invention, there is provided a bioamplifier that comprises an analog circuit that includes a series arrangement of a high pass filter, an open-loop differential amplifier, and a low pass filter. The amplifier is configured to operate below saturation, and this can be done, for example, using a current-ratio design for the amplifier.

In accordance with yet another aspect of the invention, there is provided a bioamplification method that includes the steps of (a) high pass filtering an input signal obtained from neural tissue via an electrode, (b) amplifying the filtered input signal using an amplifier operating as open-loop for at least frequencies above a lower base frequency, and (c) low pass filtering the amplified input signal.

BRIEF DESCRIPTION OF THE DRAWINGS

Preferred exemplary embodiments of the invention will hereinafter be described in conjunction with the appended drawings, wherein like designations denote like elements, and wherein.

DETAILED DESCRIPTION OF THE PREFERRED EMBODIMENTS

Described below is an embodiment of an open-loop preamplifier circuit that can be used as an implantable front-end bioamplifier for accurate acquisition of biopotentials in an animal body. The low noise figure (<100 nV/√Hz) and extremely low-power consumption (<2 μW) allows for its use in applications such as medical instrumentation, implantable neural recording systems, neuroprostheses, and game interfaces. Other suitable uses will be apparent to those skilled in the art.

Figure 1:
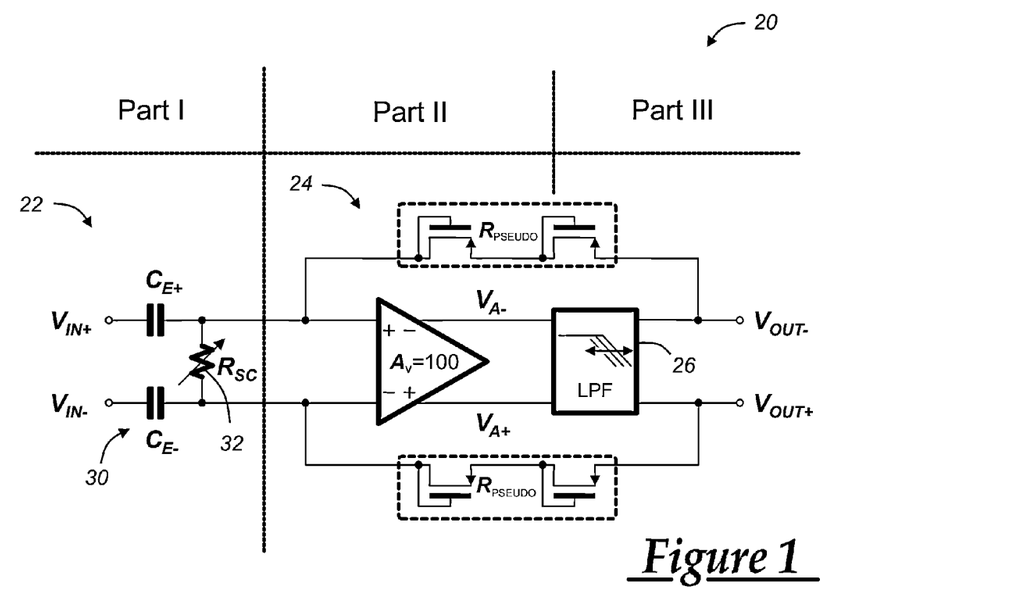
FIG. 1 is a block diagram of an embodiment of a bioamplifier constructed in accordance with the invention.

Referring to FIG. 1, the bioamplifier 20 consists of three parts: an input high pass filter (HPF) 22, an open-loop amplifier 24, and an output low pass filter (LPF) 26. Open-loop amplifier 24 is in reality a pseudo open-loop preamplifier in that it has unity gain feedback at very low frequencies, but operates in an open-loop mode at frequencies above this. As will be discussed below, the open-loop preamplifier 24 can retain a high linearity and stable operation over process and bias variations. The input and output filters 22, 26 together provide a bandpass filter for the bioamplifier 20. The input HPF 22 is a switched-capacitor (S-C) HPF and the output LPF 26 is an embedded $g_m$-C LPF. In the HPF 22 the on-chip area required is kept small by utilizing the intrinsic parasitic capacitance in the electrode to which the input filter is attached in use. Suitable electrodes such as are made from titanium are known to those skilled in the art. The cut-off frequency for HPF 22 is programmed by changing S-C frequency ($F_{SC}$). In the $g_m$-C LPF 26, the high cut-off frequency can be tuned by the transconductance gain ($g_m$) in the output stage. These and other features of bioamplifier 20 will be described below.

Figure 2:
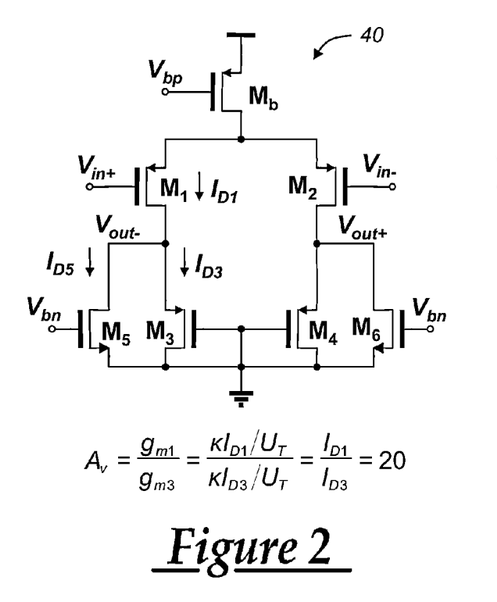
FIG. 2 is a schematic of a first stage of an open-loop amplifier used in the bioamplifier of FIG. 1.
Figure 3:
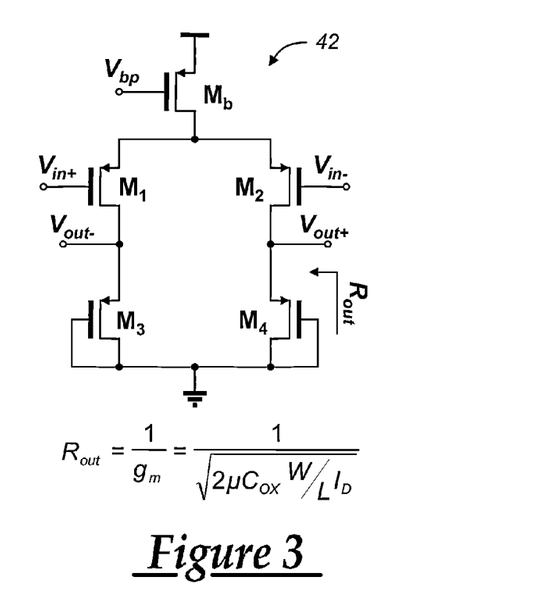
FIG. 3 is a schematic of a second and third stage of the open-loop amplifier used in the bioamplifier of FIG. 1.

The programmable S-C HPF 22 utilizes the parasitic capacitance 30 of the electrode ($C_E$) as well as the S-C resistor ($R_{SC}$) 32. The S-C HPF 22 can provide a relatively accurate frequency response because $R_{SC}$ can be easily controlled by S-C frequency ($F_{SC}$). Large parasitic electrode capacitance ($C_E$) is used to cut off the DC interference at the electrode-tissue interface. The open-loop preamplifier 24 is implemented as a fully differential amplifier that can be used to amplify weak brain signals. The overall amplifier 24 has three stages to provide the total gain of one hundred: a gain of twenty from the first stage and another five from the second and third stages together. FIG. 2 depicts an embodiment of the first preamplifier stage 40 that provides a gain of twenty, and FIG. 3 depicts the circuit 42 used for the second and third stages, each of which provides a gain of √5 for a total gain of five between the two identical stages. It should be noted that the feedback path through the $R_{pseudo}$ (shown in FIG. 1) acts as a unit gain feedback only in the very low frequency range because it forms a low-pass filter with $C_E$. The feedback factor, β, can be given as $1/(1+sR_{pseudo}C_E)$. As a result, the preamplifier 24 operates as a simple open-loop amplifier above $\omega=1/R_{pseudo}C_E$. For the LPF 26, the output impedance ($=1/g_m$) of the third stage preamplifier forms an embedded $g_m$-C LPF. By adjusting the bias current of the third stage (thus changing $g_m$), the bioamplifier 20 can eliminate any undesirable noise signals above the cut-off frequency.

Linearity is one of the main concerns in open-loop topology. To provide high linearity while maintaining the same power-noise efficiency, the first stage of the amplifier 24 can be implemented using a current-ratio design that uses transistors operating in a subthreshold region below saturation. In particular, preamplifier 24 utilizes diode-connected load transistors operating in weak inversion region at the first stage (FIG. 2). In the following stages, the transistors are operating in strong inversion (dimension-ratio design) to minimize any noise contribution. Because the gain of the first stage is set by the current ratio between the input and load transistors, current-steering sources ($M_{5,6}$) are used to accurately set the gain:

$$A_v = \frac{g_{m1}}{g_{m3}} = \frac{\kappa I_{D1}/U_T}{\kappa I_{D3}/U_T} = \frac{I_{D1}}{I_{D3}} = 20,$$

where $I_{D1}=I_{D3}+I_{D5}$ with $I_{D3}=0.05I_{D1}$ and $I_{D5}=0.95I_{D1}$. The first stage consumes the most of the supply current ($I_{D1}:I_{D7,11}=10:1$) to give high power-noise performance. To minimize any possible process mismatches, PMOS transistors can be used for both input ($M_1$, $M_2$) and load ($M_3$, $M_4$) transistors. Long-channel transistors (L=100 μm) can be used for current-steering sources ($M_{5,6}$) to reduce gain offsets, as is explained below. If desired for a particular application, a programmable gain for the preamplifier 24 can be provided by controlling the current of the nMOS current source implemented by $M_{5,6}$. Also, because the noise performance is set by the first stage 40, subsequent stages can be implemented using a different number of stages than shown and/or a different number of nMOS transistors without degradation of the noise performance.

The power-noise efficiency can be analyzed by input-referred noise in the first stage since the noise contributed from the following stages is negligible due to the high gain of the first stage. Here, the input-referred noise can be given by the EKV model (from C. Enz, F. Krummenacher, and E. Vittoz, "An analytical MOS transistor model valid in all regions of operation and dedicated to low-voltage and low-current applications," Analog Integrated Circuits and Signal Processing, vol. 8, pp. 83-114, 1995) as:

$$\overline{v_n^2} = \frac{4kT}{\kappa \cdot g_{m1}}\left(1 + \alpha_3 \frac{I_{D3}}{I_{D1}} + \frac{4\kappa}{3}\alpha_5 \frac{I_{D5}}{I_{D1}}\right) \approx \frac{4kT}{\kappa \cdot g_{m1}}\left(1 + \frac{1}{A_{V1}} + \frac{4\kappa}{3}\frac{1}{\sqrt{IC_5}}\right)$$

where $\alpha_n=2/(1+\sqrt{1+4*IC_n})$, κ is the subthreshold gate coupling coefficient, and IC is inversion coefficient which is inversely proportional to the W/L ratio of transistors. In this analysis, 1/f noise is not included because 1/f noise can be suppressed by other techniques using a chopper as will be discussed below. However, useful design criteria can be drawn from the equation given above. In order to minimize the input-referred noise, the gain in the first stage should be maximized, and the W/L ratio of $M_5$ and the $g_m$ of the rest of transistors be minimized to reduce their noise contribution. In the disclosed embodiment, the pseudo open-loop topology is used to meet all the design criteria without introducing instability. The gain of the first stage 40 is set to be twenty and the W/L of $M_5$ to be 1/100. By design, all the rest of transistors are operating in strong inversion except for the first stage. Simulation results have shown that the input-referred noise of the bioamplifier 20 is 78.4 nV/√Hz with a noise efficiency factor (NEF) of 2.3 for $I_{total}=400$ nA.

Figure 4:
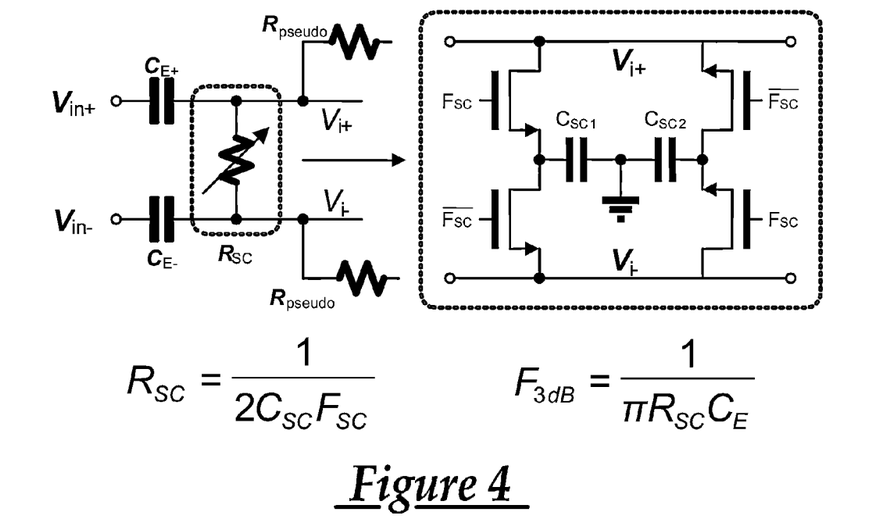
FIG. 4 is a schematic showing one implementation of a high pass filter used in the bioamplifier of FIG. 1.

In neural signal monitoring low frequency signals should be cut off to suppress the electrode offset voltage and drift. FIG. 4 shows the S-C HPF 22 that can be implemented by utilizing the electrode capacitance ($C_E$). Typically, the electrode capacitance is relatively large (>5 nF), therefore, a low cut-off frequency (<0.1 Hz) can be implemented without using an external capacitor. The cut-off frequency can be controlled by an RC network formed by $C_E$ and $R_{SC}$ where the S-C resistance ($R_{SC}$) is determined by $F_{SC}$ and $C_{SC}$. To minimize the impedance mismatch and charge injection in the differential signal lines, the paired $R_{SC}$ can be switched by quadrature phases. The cut-off frequency can be programmed by adjusting the S-C frequency, $F_{SC}$. Combined with the embedded $g_m$-C LPF at the third gain stage, a complete bandpass filter is formed for the bioamplifier 20. This bandwidth programmability allows the proposed amplifier to be applied for various neural interface applications, such as EEG, ECoG, local field potential, neuroprostheses, BCI, etc.

Figure 5:
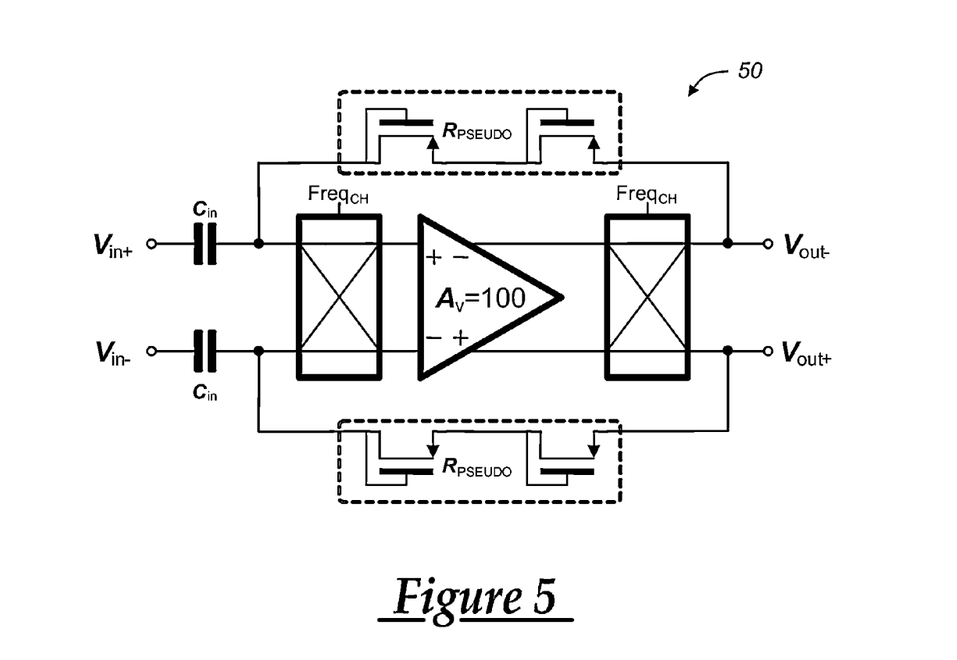
FIG. 5 is a block diagram of a chopper stabilized preamplifier that can be used in place of the preamplifier of FIG. 1 to obtain improved noise suppression.

In addition to thermal noise, 1/f (or flicker) noise can severely interfere with the low-frequency neural signals in EEG and ECoG applications. To reduce the 1/f noise, large PMOS transistors (W/L=200 μm/1 μm) were used in the first stage. PMOS transistors typically show better noise performance than NMOS counterparts. However, there can still be relatively large 1/f noise from $M_{3,4}$ which is designed to be relatively small in order to optimize the gain and bandwidth. To suppress the 1/f noise furthermore, a chopper can be used as shown in FIG. 5. Thus, the chopper stabilized amplifier circuit 50 of FIG. 5 can be used in place of the amplifier 24 of FIG. 1.

Figure 6:
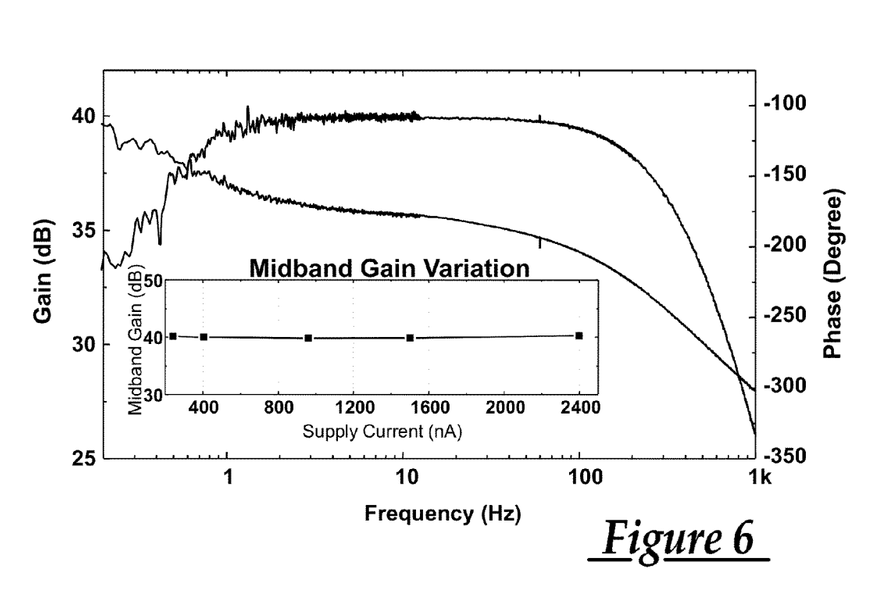
FIG. 6 is a plot of the frequency response and midband gain variation for a fabricated implementation of the bioamplifier of FIG. 1.
Figure 7:
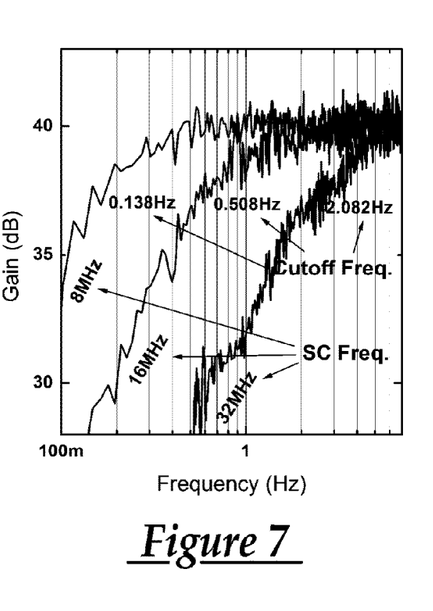
FIG. 7 is a plot of the frequency response of the high pass filter used in the fabricated bioamplifier.
Figure 8:
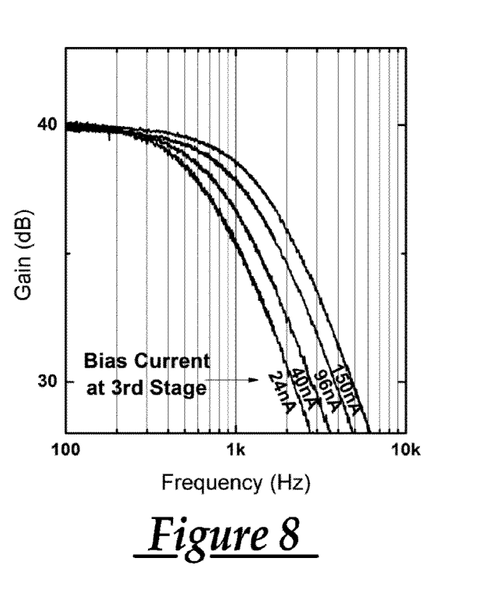
FIG. 8 is a plot of the frequency response of the low pass filter used in the fabricated bioamplifier.
Figure 9:
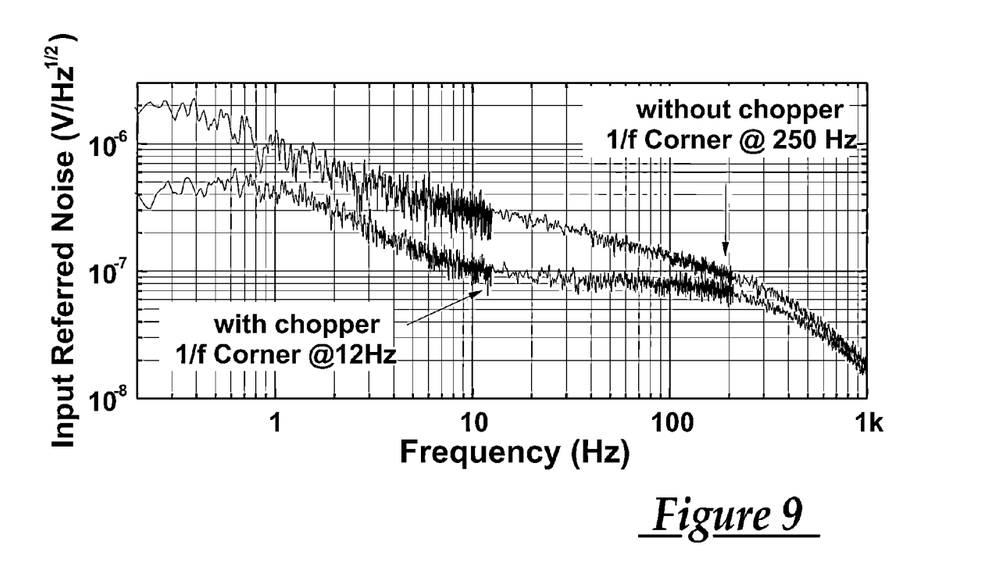
FIG. 9 shows the input-referred noise of fabricated bioamplifiers with and without chopper stabilization.
Figure 10:
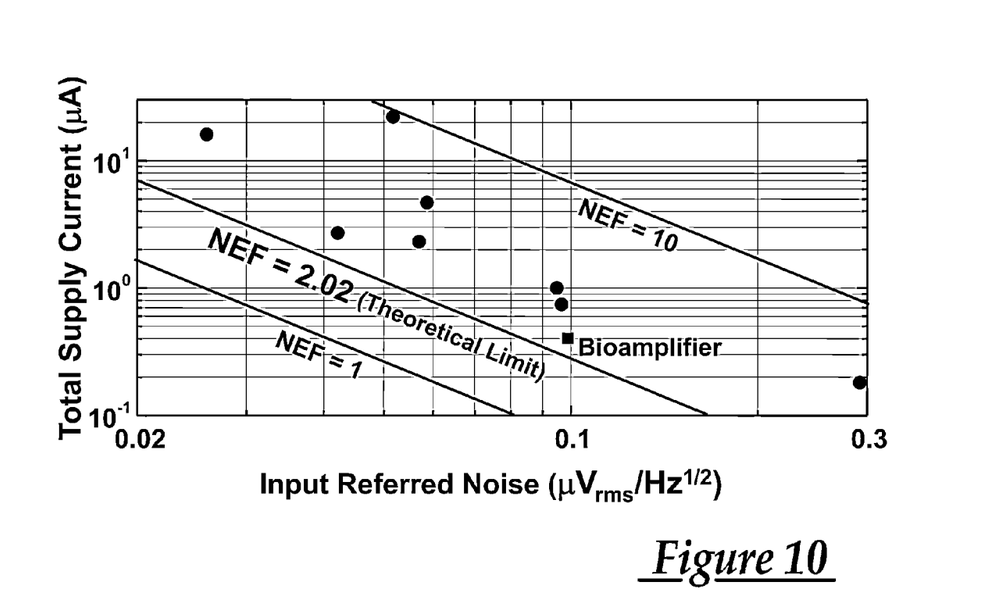
FIG. 10 is a noise efficiency factor (NEF) comparison graph of various amplifiers.

An actual bioamplifier 20 was fabricated and tested using 0.25 μm 1P5M CMOS process. The overall power consumption of the fabricated device was 1 μW (400 nA at 2.5V supply). FIG. 6 shows the measured frequency response of the fabricated bioamplifier. It shows a stable mid-band gain of 40.01±0.2 dB for various supply currents from 240 nA to 2400 nA. To verify the process variation, the gain variation was measured from twenty chips for which a variation of 39.95±0.53 dB was observed. These results show that the bioamplifier 20 has a stable gain over the bias and process variation. And by programming the switched-capacitor frequency and bias current, the bandwidth of the preamplifier can be controlled from 138 mHz to 2.2 kHz to meet various application requirements. FIG. 7 shows the frequency response of the S-C HPF 22. To verify the operation, the electrode capacitance ($C_E$) was taken to be 10 μF in 20 mm² and S-C capacitance ($C_{SC}$) was 1 pF. By changing the S-C frequency between 8, 16, and 32 MHz, the cut-off frequency could be modulated to 0.13, 0.598, and 2.082 Hz, respectively. FIG. 8 shows the frequency response of the programmable $g_m$-C filter 26 for various bias currents in the third stage from 24 nA to 150 nA. FIG. 9 shows the measured input-referred noise both with and without the chopper stabilization of the preamplifier 24. By enabling the chopper, 1/f corner frequency was reduced by twenty times from 250 Hz to 12 Hz. FIG. 10 shows the noise performance of the bioamplifier 20 (marked by a square) compared with that of various known different designs (marked by circles). Performance of the fabricated bioamplifier 20 is summarized in Table 1.

TABLE I

| Parameter | Measured |
| --- | --- |
| Technology | 0.25 μm 1P5M CMOS |
| Supply Voltage | 2.5 V |
| Total Current | 0.4 μA |
| Gain (Average ± σ, 20 chips) | 39.95 ± 0.53 dB |
| Bandwidth | 0.51~292 Hz |
| Input-referred Noise | 1.69 μVrms |
| Noise Efficiency Factor | 2.43 |
| THD | <1% (2.25mVpp @ 100 Hz) |
| Dynamic Range | 53.5 dB |

TABLE I-continued

| Parameter | Measured |
| --- | --- |
| CMRR | 79 dB |
| PSRR | 82 dB |
| Area | 0.043 mm² |

Figure 11:
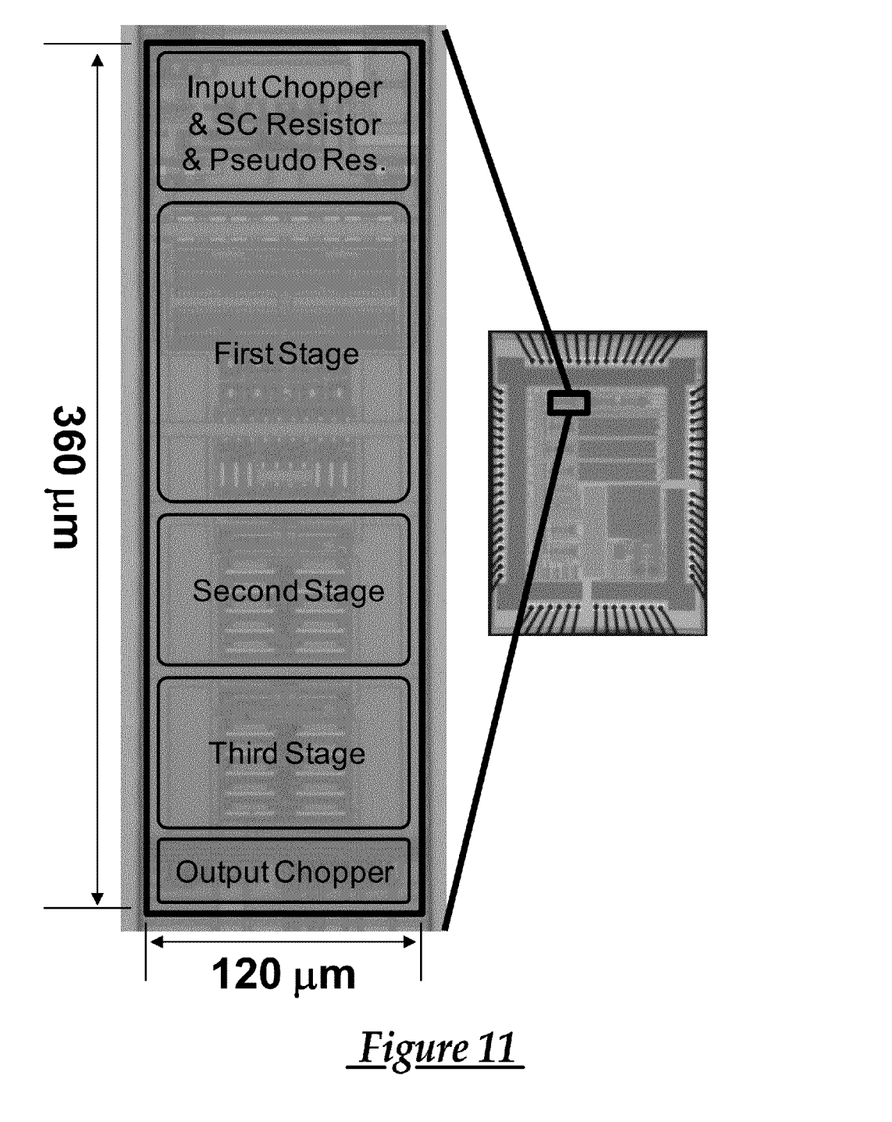
FIG. 11 is a microphotograph of the fabricated bioamplifier.

The measured thermal noise level was 85 nV/√Hz and the input-referred noise was 1.69 μVrms from 0.3 Hz to 1 kHz. The fabricated bioamplifier achieved an NEF value of 2.43. The total harmonic distortion (THD) was measured to be below 1% when an input signal of 2.25 mV @ 100 Hz was applied. The measured CMRR and PSRR were 79 dB and 82 dB, respectively, and the dynamic range was 53.5 dB. The fabricated bioamplifier occupies the small area of 0.043 mm². A microphotograph of the bioamplifier 20 is shown in FIG. 11.

Figure 12:
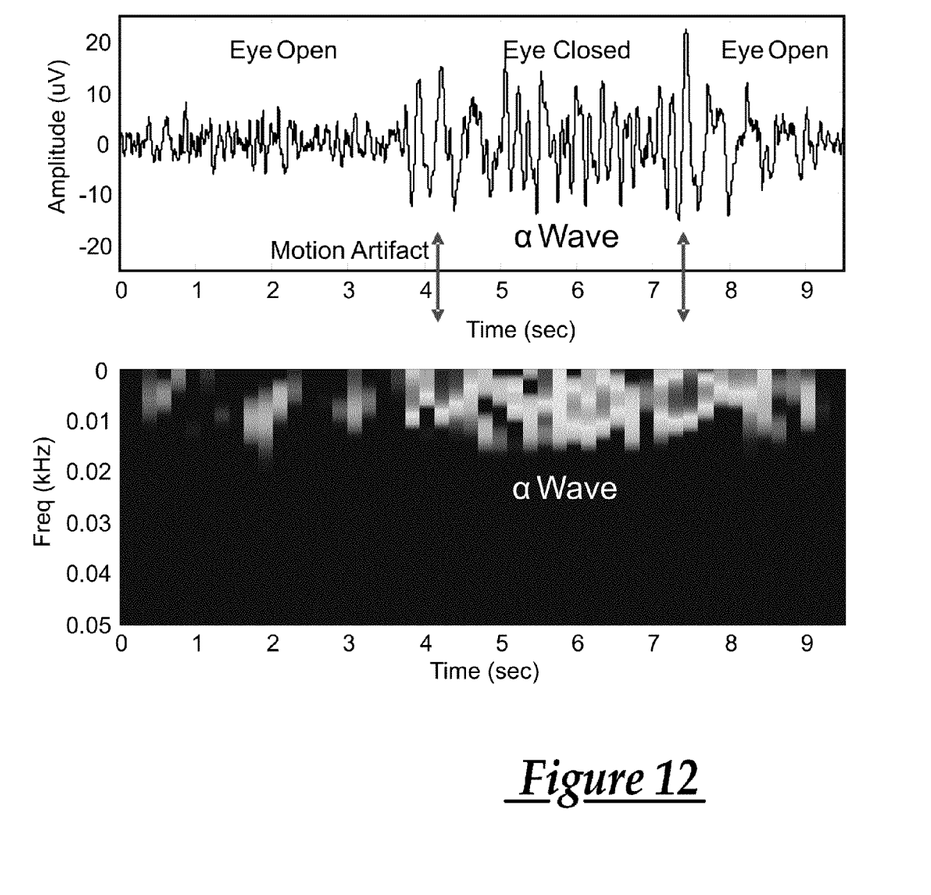
FIG. 12 shows the recorded waveform and its spectrogram of the results of in vivo testing of the fabricated bioamplifier.

To evaluate the performance of the fabricated preamplifier, in-vivo EEG signals of a human subject have been measured. FIG. 12 shows the recorded waveform and its spectrogram of a subject while blinking the eyes. During eye-closed periods, α-waves in 8-12 Hz bandwidth were observed which is a typical brain activity in the absence of visual stimulus. Eye lid motion artifact can be distinctly shown during the recording session indicated by the arrows in FIG. 12.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. For example, rather than using the LPF 22, an AC-coupled input capacitor could be used which could provide a simpler circuit implementation, albeit at some cost of chip area. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A bioamplifier, comprising:
a high pass filter having an input and a filter output;
an amplifier coupled to the filter output and having an amplifier output; and
a low pass filter coupled to the amplifier output, wherein an output of the low pass filter provides feedback to the amplifier at lower frequencies such that the amplifier receives feedback at lower frequencies and otherwise operates in an open-loop mode at higher frequencies.

2. A bioamplifier as defined in claim 1, wherein the high pass filter includes a switched capacitor resistance.

3. A bioamplifier as defined in claim 1, wherein the high pass filter includes a capacitor from an electrode.

4. A bioamplifier as defined in claim 3, wherein the capacitor comprises parasitic capacitance of the electrode.

5. A bioamplifier as defined in claim 1, wherein the high pass filter includes an AC coupled input capacitor.

6. A bioamplifier as defined in claim 1, wherein the high pass filter has a cut-off frequency determined by a frequency of a signal applied to the input.

7. A bioamplifier as defined in claim 1, wherein the open-loop amplifier further comprises a chopper stabilized amplifier.

8. A bioamplifier as defined in claim 1, wherein the open-loop amplifier includes a differential pair of transistors.

9. A bioamplifier as defined in claim 8, wherein at least one transistor is configured to operate below saturation.

10. A bioamplifier as defined in claim 1, wherein the open-loop amplifier includes a differential input and a differential output.

11. A bioamplifier as defined in claim 1, wherein the open-loop amplifier has a gain determined by a current source.

12. A bioamplifier as defined in claim 11, wherein the current source is programmable.

13. A bioamplifier as defined in claim 1, wherein the lower frequency feedback operates at frequencies below 1/RC and the amplifier operates as open-loop at frequencies above 1/RC, where R is the resistance in the feedback and C is the capacitance in the high pass filter.

14. A bioamplifier, comprising an analog circuit that includes a series arrangement of a high pass filter, an open-loop differential amplifier, and a low pass filter, the amplifier configured to operate below saturation and consume less than 5 µW, wherein the high pass filter, the open-loop differential amplifier, and the low pass filter occupy an area that is equal to or smaller than $5 \times 10^{-7}$ m$^2$.

15. A bioamplifier as defined in claim 14, wherein the high pass filter has an input and a cut-off frequency determined by a frequency of a signal applied to the input.

16. A bioamplifier as defined in claim 14, wherein the high pass filter includes a switched capacitor resistance.

17. A bioamplifier as defined in claim 14, wherein the high pass filter includes a capacitor from an electrode.

* * * * *